(12) United States Patent
Jach et al.

(10) Patent No.: US 6,280,605 B1
(45) Date of Patent: Aug. 28, 2001

(54) ELECTROCHEMICAL SENSOR

(75) Inventors: Olaf Jach, Boeblingen; Johann Riegel, Bietigheim-Bissingen; Lothar Diehl, Stuttgart, all of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/220,433

(22) Filed: Dec. 24, 1998

(30) Foreign Application Priority Data

Dec. 24, 1997 (DE) ................................. 197 57 824
Aug. 19, 1998 (DE) ................................. 198 37 607

(51) Int. Cl.⁷ ..................................... G01N 27/407
(52) U.S. Cl. .................. 205/784.5; 204/425; 204/426; 204/427
(58) Field of Search .................... 204/421–429; 205/783, 784, 784.5, 785

(56) References Cited

U.S. PATENT DOCUMENTS

| | | | |
|---|---|---|---|
| 4,579,643 | * 4/1986 | Mase et al. | 204/426 |
| 4,798,693 | * 1/1989 | Mase et al. | 204/426 |
| 5,108,577 | * 4/1992 | Mase et al. | 204/426 |
| 5,130,002 | * 7/1992 | Murase et al. | 204/425 |
| 5,496,461 | * 3/1996 | Hotzel et al. | 204/426 |
| 5,529,677 | * 6/1996 | Schneider et al. | 204/425 |
| 5,787,866 | * 8/1998 | Sugiyama et al. | 204/426 |
| 5,880,406 | * 3/1999 | Gerstel et al. | 204/426 |
| 5,985,118 | * 11/1999 | Makino et al. | 204/426 |

* cited by examiner

*Primary Examiner*—T. Tung
(74) *Attorney, Agent, or Firm*—Kenyon & Kenyon

(57) ABSTRACT

An electrochemical sensor measures a gas concentration of a measured gas with an electrochemical element. The electrochemical sensor includes an electrochemical pump cell with a first solid electrolyte body, a first and a second electrode, and a gas chamber, which is connected to a measured gas chamber via a gas inlet opening and in which one of the two electrodes is located. The electrochemical sensor also includes a second solid electrolyte body with an electrochemical sensor cell (e.g., a Nernst cell), which has a third electrode and a reference gas chamber in which a fourth electrode is located, with the electrodes having a supply conductor for electrical contacting. A supply conductor of the fourth electrode is provided with an electrically insulating layer to insulate it against the second solid electrolyte body.

17 Claims, 4 Drawing Sheets

ELECTROCHEMICAL SENSOR

FIELD OF THE INVENTION

The present invention relates to an electrochemical sensor, and to a use of the electrochemical sensor in determining a lambda value of a gas mixture.

BACKGROUND INFORMATION

Conventional electrochemical sensors generally include an electrochemical element which has an electrochemical pump cell with a preferably flat first solid electrolyte body and first and second preferably porous electrodes. These conventional sensors further include an electrochemical sensor cell which interacts with the pump cell and has a preferably flat second solid electrolyte body and a third and a fourth preferably porous electrode. The electrochemical sensor also has a gas inlet opening and a gas inlet duct, which is connected at one end to a measured gas chamber. The other end of the gas inlet duct opens into a cavity, also referred to as a gas chamber, lying inside the electrochemical element. The second and third electrodes and preferably one diffusion resistor arrangement are located in the gas chamber. The diffusion resistor arrangement can be formed by a porous filling. The measured gas enters the cavity via the gas inlet opening and the gas inlet duct, with the first and second electrodes of the pump cell regulating the entry of the measured gas into the gas chamber. This produces a controlled partial pressure of the gas component to be measured. The electrochemical potential difference between the electrodes of the second solid electrolyte body (which is due to the different partial pressures of the gas in the diffusion resistor arrangement and in a reference gas chamber located, for example, in the second solid electrolyte body) can be detected by a detecting device, such as a voltmeter unit, positioned outside the electrochemical element.

Conventional electrochemical sensors are also used in applications such as catalytic emission control in internal combustion engines under. These electromechanical sensors are designated in the industry as "flat broadband lambda sensors".

One of the disadvantages of the conventional electrochemical sensors is that they demonstrate elevated ripple during a lambda=1 pass, especially at high operating temperatures. This leads to problems, especially in control processes where the lambda value represents the controlled variable. Due to the ripple in the lambda signal, it is sometimes not possible to set an adequately stable output quantity.

SUMMARY OF THE INVENTION

An electrochemical sensor according to the present invention has an electrochemical element for measuring a gas concentration of a measured gas. The sensor includes an electrochemical pump cell with a first solid electrolyte body, first and second electrodes, and a gas chamber which is connected to a measured gas chamber via a gas inlet opening. An electrochemical sensor cell (e.g., a Nernst cell) is also provided which has a second solid electrolyte body, a third electrode, and a reference gas chamber in which a fourth electrode is located. The electrodes have a supply conductor for an electrical contacting.

According to the present invention, the supply conductor to the fourth electrode is provided with an electrically insulating layer to insulate this supply conductor against the second solid electrolyte body. A resistive coupling of the electrode supply conductors in conventional electrochemical sensors can cause the pump voltage to interfere with the Nernst voltage of the sensor cell. Especially at high operating temperatures, this can be one reason for the known (however unwanted) phenomenon of lambda=1 ripple (e.g., transients during abrupt gas change).

According to the present invention, a resistive decoupling of the supply conductor to the fourth electrode from the solid electrolyte body, and therefore from the other electrode supply conductors as well, advantageously reduces the lambda=1 ripple and can also eliminate it. This improves the controller dynamics of the electrochemical sensor according to the present invention as compared to that of the conventional electrochemical sensors.

In another embodiment of the present invention, the layer is made of aluminum oxide or contains aluminum oxide.

In another embodiment of the present invention, the layer (e.g., an insulation material used for resistive decoupling) is attached to the solid electrolyte body or the electrode supply conductor in the form of a printed layer.

In another embodiment of the present invention, the layer is at least as wide as the supply conductor of the fourth electrode. Alternatively, the layer can be the same width as a reference gas duct containing the supply conductor of the fourth electrode and assigned to the reference gas chamber. The electrically insulating layer is positioned between the supply conductor and a wall of the reference gas chamber located in the second solid electrolyte body.

In another embodiment of the present invention, the supply conductor of the fourth electrode is much narrower than the reference gas duct. This additionally prevents the pump voltage from interfering with the Nernst voltage, since the supply conductor has a small surface area.

The electrochemical sensor according to the present invention and its electrochemical element are produced in a suitable manner by starting with oxygen-conducting, wafer-shaped or film-like solid electrolytes, made for example of stabilized zirconium dioxide, and coating both sides with an inner and an outer pump electrode having conductor paths which represent the supply conductors for electrical contacting. The resistive layer according to the present invention is applied between the conductor paths and the solid electrolyte film. Thus, the conductor paths are preferably applied to the layer. The inner pump electrode is advantageously located in the edge region of a diffusion or gas inlet duct through which the measured gas is supplied. The gas inlet duct can be designed as a gas diffusion resistance. The pump cell obtained in this manner can then be laminated and sintered to a sensor cell (Nernst cell), produced in a similar manner and made from a second solid electrolyte film and to a third, solid electrolyte film that may be designed as a heater unit.

The porous fillings (for example, the diffusion barriers in the gas chamber) are produced by using, in particular, porously sintered film inserts made of a ceramic material which has suitable thermal expansion characteristics which are identical or similar to the those of the solid electrolyte films used. A film insert made of the same ceramic material from which the solid electrolyte films are produced is preferably used for the filling. The porosity of the insert can be generated by pore-forming substances such as thermal carbon black powder, organic plastics, or salts. These pore-forming substances burn up, decompose, or evaporate during sintering.

The present invention also relates to broadband lambda sensors for determining the lambda value of gas mixtures in internal combustion engines. The lambda value, or "air ratio", is defined as the ratio between the instantaneous air/fuel ratio and the stoichiometric air/fuel ratio. The sensors measure the oxygen content of the exhaust gas via a limit current variation.

DETAILED DESCRIPTION

Figure 1:
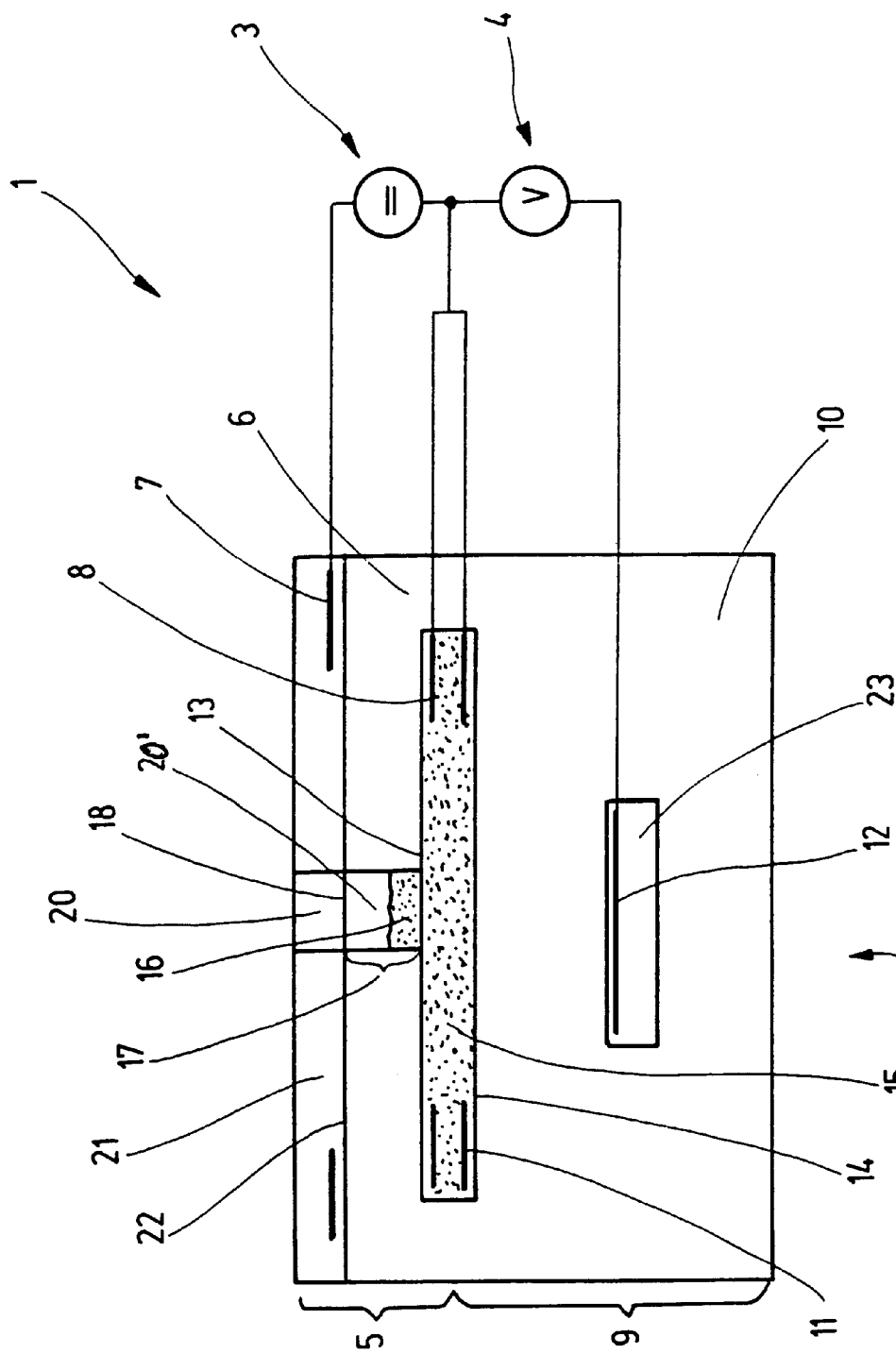
FIG. 1 shows a sectional view of a first embodiment of a sensor according to the present invention.

FIG. 1 shows a cross section of an electrochemical sensor 1 which has an electrochemical element 2, a voltage supply unit 3 as a power supply system, and an evaluator which can be implemented as a voltmeter 4.

Figure 2:
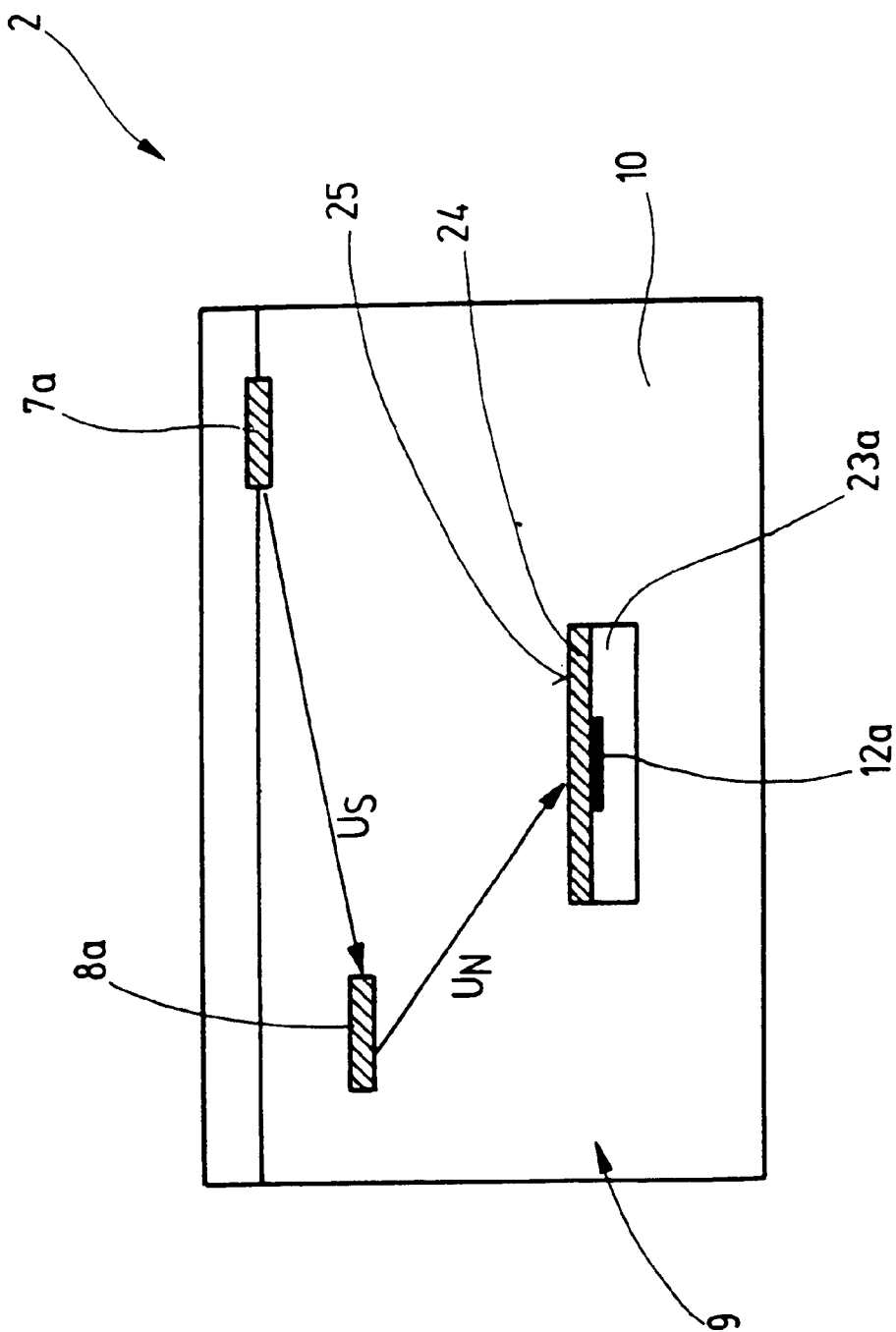
FIG. 2 shows a sectional view of the sensor illustrated in FIG. 1, with a sectional plane extending parallel to a sectional plane illustrated in FIG. 1.

Electrochemical element 2 has an electrochemical pump cell 5 which includes a first flat solid electrolyte body 6, a first porous electrode 7, and a second porous electrode 8. Electrodes 7 and 8 are preferably ring-shaped and each extend from electrochemical element 2 over supply conductors 7a and 8a, respectively, (as shown in FIG. 2) for the purpose of electrical contacting. Supply conductor 7a is assigned to first electrode 7. Supply conductor 8a is used as a supply conductor for second electrode 8 and for a third electrode 11, which can also be ring-shaped.

Electrochemical element 2 also has an electrochemical sensor cell 9 (e.g., a Nernst cell) which includes a second solid electrolyte body 10, and third and fourth electrodes 11, 12. Fourth electrode 12 extends from electrochemical element 2 over supply conductor 12a (shown in FIG. 2).

Electrochemical pump cell 5 is supplied with power at first and second electrodes 7 and 8 by external voltage supply unit 3. However, a power supply unit can also be provided as an alternative.

First and second solid electrolyte bodies 6 and 10 are connected to one another and surround an inner cavity 14, also referred to as a gas chamber. This chamber is completely or partially filled with a porous material 15 and contains second and third electrodes 8 and 11. Inner cavity 14 comes into contact with measured gas 19 via a gas inlet duct 17 that is partially filled with a porous filling 16. A porous covering 20, which can be part of a porous protective layer 21, can be positioned over gas inlet opening 18. This protective layer 21 is attached to a surface 22 of first solid electrolyte body 6 facing a measured gas chamber 19, and therefore covers first electrode 7 of the pump cell.

Second solid electrolyte body 10 has a reference gas chamber 23. A reference gas duct 23a (shown in FIG. 2) is associated with reference gas chamber 23, through which a comparison gas, also referred to as a reference gas, can be conducted to reference gas chamber 23.

From measured gas chamber 19, the measured gas enters inner cavity 14 via gas inlet opening 18 and gas inlet duct 17, with a controlled partial pressure being set by pumping oxygen in and out using the pump voltage applied to first and second electrodes 7 and 8 of pump cell 5. Power, or voltage, is supplied to pump cell 5 by voltage supply unit 3 mounted outside electrochemical element 2, as described above.

Due to the different partial pressures of the gas in gas chamber 13 as well as in reference gas chamber 23 located in second solid electrolyte body 10, an electrochemical potential difference is produced between third and fourth electrodes 11 and 12 of sensor cell 9. This potential difference is detected by voltmeter 4 positioned outside the electrochemical element. It is also possible to provide an evaluator in this embodiment.

Covering 20 and hollow space 20' located beneath it prevent liquid and solid components contained in the measured gas from entering. These components can be, for example, gasoline or particles of soot in the exhaust gas of an internal combustion engine. They also prevent this gasoline from entering gas chamber 13 via the gas inlet opening and gas inlet duct.

FIG. 2 shows a simplified sectional view of electrochemical sensor 2 from FIG. 1, with the sectional plane lying parallel to the drawing plane shown in FIG. 1. Reference gas duct 23a contains an electrically insulating layer 24. This layer 24 is assigned to top 25 of reference gas duct 23a. As shown in FIG. 2, layer 24 extends across the entire width of reference gas duct 23a. It is also possible for layer 24 to have the same width as supply conductor 12a of fourth electrode 12, also referred to as the reference electrode. Supply conductor 12a is mounted in a way that provides electrical insulation against solid electrolyte body 10. To achieve this, the width chosen for layer 24 should be as least equal to that of supply conductor 12a.

In another embodiment, layer 24 is produced from a printed layer of aluminum oxide ($Al_2O_3$), which, during production of element 2, is applied to the solid electrolyte body or supply conductor 12a in the form of a paste and subsequently sintered. This printed layer, which is preferably dense-sintered, also prevents exhaust gas (measured gas) or gasoline from being conducted to reference gas duct 23a. This is achieved by having layer 24 cover the entire width of reference gas chamber 23a, as discussed above. Protective layer 24 extends along the entire length of supply conductor 12a.

It is also possible to design layer 24 as a porous, electrically insulating layer. FIG. 2 also shows that supply conductor 12a can be much narrower than reference gas duct 23a.

Electrically isolating layer 24 provides resistive decoupling of supply conductors 12a from 8a or 7a, preventing pump voltage $U_S$ from interfering with the sensor voltage or Nernst voltage $U_n$ of sensor cell 9. This yields an output signal of sensor cell 9, which demonstrates especially low ripple. This means that the lambda=1 ripple is at least reduced.

Figure 3:
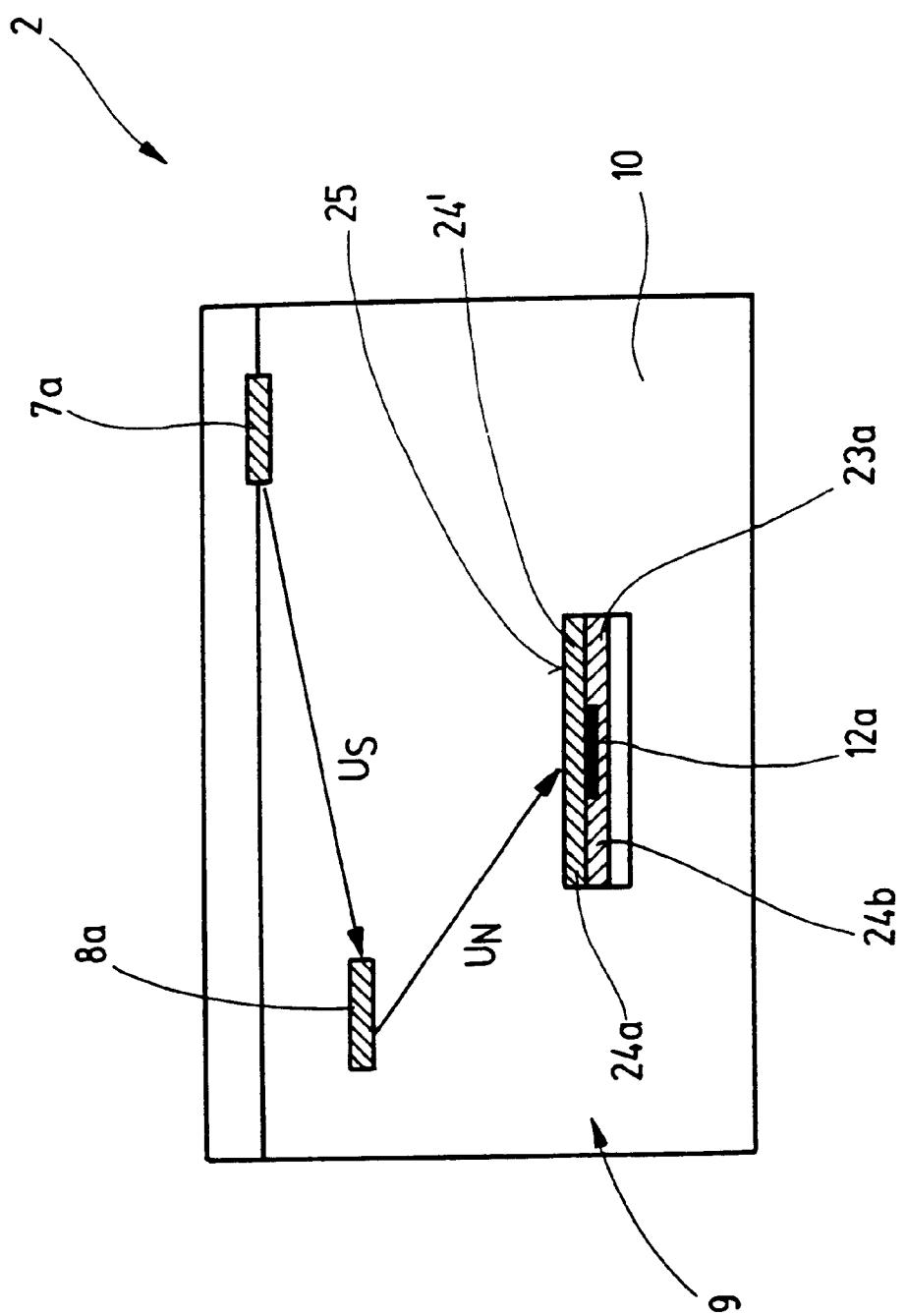
FIG. 3 shows a sectional view of a second embodiment of the sensor according to the present invention, with its sectional plane extending parallel to the sectional plane illustrated in FIG. 1.

FIG. 3 shows a second embodiment for resistive decoupling of supply conductors 12a from 8a or 7a, so that, as described above, pump voltage $U_S$ cannot interfere with the sensor voltage or Nernst voltage $U_n$ of sensor cell 9 (shown in FIG. 1). The resistive decoupling arrangement is designed so that supply conductor 12a is completely surrounded by an electrically insulating layer 24'. Layer 24' can be formed by two partial layers 24a and 24b, with layer 24a being assigned to top 25 of reference gas duct 23a, similarly to layer 24 shown in FIG. 2. Supply conductor 12a for fourth electrode 12 is attached to the side of layer 24a facing away from top 25 of the reference gas duct. Electrically insulating layer 24b is attached to layer 24a so that it completely surrounds supply conductor 12a. FIG. 3 shows that the width of layer 24' or layers 24a and 24b covers the entire width of reference gas duct 23a.

Layer 24' can be produced as a porous or as a dense-sintered insulation layer made of aluminum oxide ($Al_2O_3$) or containing aluminum oxide. If layer 24' is designed as a porous insulating layer, supply conductor 12a is preferably provided with a gas-tight barrier against layer 24' so that supply conductor 12a will not increase the active surface area of electrode 12. This could result in an unwanted influence on the sensor voltage or Nernst voltage $U_n$ of sensor cell 9.

Figure 4:
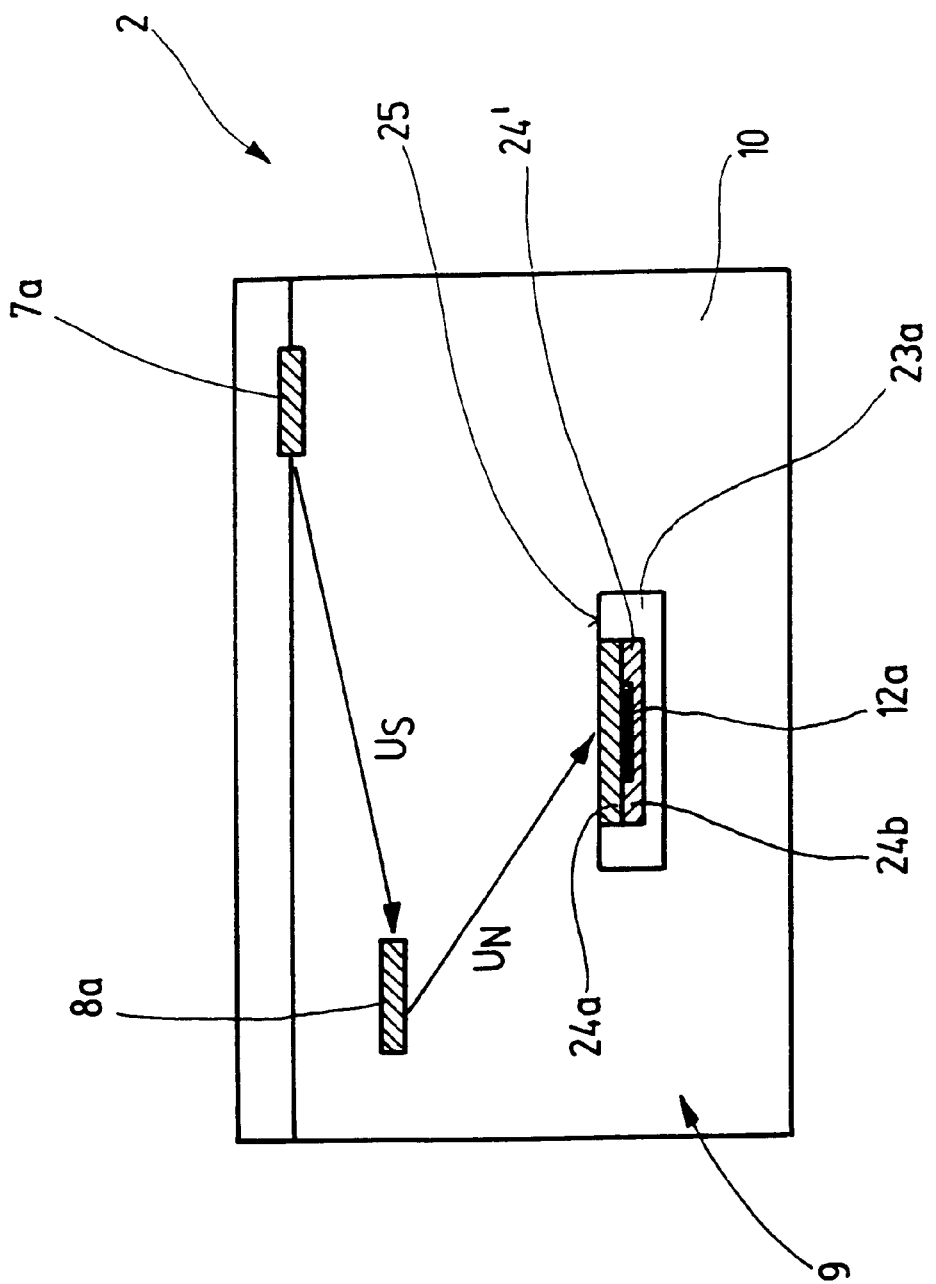
FIG. 4 shows a sectional view of a third embodiment of the sensor according to the present invention, with its sectional plane extending parallel to the sectional plane illustrated in FIG. 1.

The embodiment shown in FIG. 4 differs from the embodiment shown in FIG. 3 in that layer 24' does not cover the entire width of reference gas duct 23a. In element 2 shown in FIG. 4, layer 24' can also completely surround supply conductor 12a, i.e., layer 24' can be formed by two partial layers 24a and 24b which completely surround supply conductor 12a. However, as provided for the embodiment shown in FIG. 2, it is also possible to provide only one electrically insulating layer 24a located on top 25 of reference gas duct 23a. Electrically insulating layer 24' can be either porous or dense-sintered, as described above for the embodiments shown in FIGS. 2 and 3. If layer 24' is designed as a porous electrically insulating layer, supply conductor 12a is preferably surrounded by a gas-tight barrier also in the embodiment shown in FIG. 4, which is thus positioned between supply conductor 12a and layer 24'.

What is claimed is:

1. An electrochemical sensor including an electrochemical element for measuring a gas concentration of a gas contained in a first gas chamber, the electrochemical sensor comprising:

an electrochemical pump cell including a first solid electrolyte body, a first electrode, a second electrode and a second gas chamber, the second gas chamber communicating with the first gas chamber via a gas inlet opening, wherein one of the first electrode and the second electrode is situated in the second gas chamber; and an electrochemical sensor cell including a second solid electrolyte body, a third electrode, a reference gas chamber and a fourth electrode situated in the reference gas chamber, the reference gas chamber cooperating with a reference gas duct, the fourth electrode having a supply conductor which is provided for an electrical connection and which includes an electrically insulating layer, the electrically insulating layer being disposed, at least in part, in the reference gas duct and insulating the supply conductor from the second solid electrolyte body, wherein the reference gas chamber and the reference gas duct are inside the second solid electrolyte body and outside the first solid electrolyte body.

2. The electrochemical sensor according to claim 1, wherein the electrically insulating layer includes aluminum oxide.

3. The electrochemical sensor according to claim 1, wherein the electrically insulating layer is a printed layer coupled to one of the second solid electrolyte body and the supply conductor.

4. The electrochemical sensor according to claim 1, wherein the electrically insulating layer is dense-sintered.

5. The electrochemical sensor according to claim 1, wherein the electrically insulating layer is porous.

6. The electrochemical sensor according to claim 1, wherein the electrically insulating layer is at least as wide as the supply conductor.

7. The electrochemical sensor according to claim 1, wherein the supply conductor is situated in the reference gas duct, and wherein the electrically insulating layer has a first width which is equal to a second width of the reference gas duct.

8. The electrochemical sensor according to claim 7, wherein the supply conductor has a third width which is smaller than the second width.

9. The electrochemical sensor according to claim 1, wherein the electrically insulating layer completely surrounds the supply conductor.

10. The electrochemical sensor according to claim 9, wherein the electrically insulating layer is composed of a plurality of partial layers.

11. The electrochemical sensor according to claim 1, further comprising:

a gas-tight barrier situated between the electrically insulating layer and the supply conductor.

12. The electrochemical sensor according to claim 1, wherein the electrochemical sensor cell includes a Nernst cell.

13. The electrochemical sensor according to claim 1, wherein the electrically insulating layer provides resistive decoupling of the supply conductor from at least one of a first electrode supply conductor and a second electrode supply conductor for at least limiting a pump voltage from interfering with a sensor voltage for reducing a ripple associated with the sensor voltage.

14. The electrochemical sensor according to claim 1, wherein the electrically insulating layer provides resistive decoupling for reducing a ripple associated with the sensor voltage.

15. A method for determining a lambda value of a gas mixture in an internal combustion engine, comprising the steps of:

providing an electrochemical sensor which has an electrochemical element for measuring a gas concentration of the gas mixture contained in a first gas chamber, the electrochemical sensor including:

an electrochemical pump cell including a first solid electrolyte body, a first electrode, a second electrode and a second gas chamber, the second gas chamber communicating with the first gas chamber via a gas inlet opening, wherein one of the first electrode and the second electrode is situated in the second gas chamber, and an electrochemical sensor cell including a second solid electrolyte body, a third electrode, a reference gas chamber and a fourth electrode situated in the reference gas chamber, the reference gas chamber cooperating with a reference gas duct, the fourth electrode having a supply conductor which is provided for an electrical connection and which includes an electrically insulating layer, the electrically insulating layer being disposed, at least in part, in the reference gas duct and insulating the supply conductor from the second solid electrolyte body, wherein the reference gas chamber and the reference gas duct are inside the second solid electrolyte body and outside the first solid electrolyte body; and determining the lambda value using the electrochemical sensor.

16. The method according to claim 15, wherein the electrically insulating layer provides resistive decoupling of the supply conductor from at least one of a first electrode supply conductor and a second electrode supply conductor for at least limiting a pump voltage from interfering with a sensor voltage for reducing a ripple associated with the sensor voltage.

17. The method according to claim 15, wherein the electrically insulating layer provides resistive decoupling for reducing a ripple associated with the sensor voltage.

* * * * *